(12) United States Patent
Larche et al.

(10) Patent No.: US 9,131,946 B2
(45) Date of Patent: Sep. 15, 2015

(54) SURGICAL INSTRUMENT FOR A TECHNIQUE FOR ATTACHING BONE FRAGMENTS USING A CANNULATED SCREW

(75) Inventors: Gregoire Larche, Cholet (FR); Jean-Pierre Podgorski, Saint-Crespin-sur-Moine (FR); Sylvain Sorin, La Bruffiere (FR)

(73) Assignee: D.L.P., Haute Goulaine (FR)

( * ) Notice: Subject to any disclaimer, the term of this patent is extended or adjusted under 35 U.S.C. 154(b) by 236 days.

(21) Appl. No.: 13/993,982

(22) PCT Filed: Dec. 12, 2011

(86) PCT No.: PCT/FR2011/052942
§ 371 (c)(1),
(2), (4) Date: Jul. 23, 2013

(87) PCT Pub. No.: WO2012/080637
PCT Pub. Date: Jun. 21, 2012

(65) Prior Publication Data
US 2013/0304068 A1    Nov. 14, 2013

(30) Foreign Application Priority Data
Dec. 13, 2010 (FR) .................................... 10 60404

(51) Int. Cl.
*A61B 17/88* (2006.01)
*A61B 17/32* (2006.01)
(Continued)

(52) U.S. Cl.
CPC .............. *A61B 17/16* (2013.01); *A61B 17/888* (2013.01); *A61B 17/8875* (2013.01);
(Continued)

(58) Field of Classification Search
CPC ........... A61B 17/8875; A61B 17/8897; A61B 17/16; A61B 17/8877; A61B 17/8894
See application file for complete search history.

(56) References Cited

U.S. PATENT DOCUMENTS 2,121,193 A * 6/1938 Hanicke ........................ 606/65
2,329,398 A * 9/1943 Duffy ............................ 606/104
(Continued)

FOREIGN PATENT DOCUMENTS

CH            634742 A5    2/1983

OTHER PUBLICATIONS

International Search Report of PCT/FR2011/052942, mailing date of Mar. 9, 2012.

*Primary Examiner* — Christian Sevilla
(74) *Attorney, Agent, or Firm* — Westerman, Hattori, Daniels & Adrian, LLP (57) ABSTRACT

The present invention relates to a surgical instrument for a technique for attaching bone fragments using a cannulated screw, the implantation of which is guided by a pin. The instrument (1) comprises: (i) a central channel (5) defining a longitudinal axis (6), enabling the slidable and rotatable insertion of said instrument (1) onto said guide pin; (ii) a nesting structure (15) suitable for being inserted into a recess made in the head of said cannulated screw and for blocking the rotation thereof; (iii) cutting edges (20, 21) suitable for boring at least one of said bone fragments by rotating said surgical instrument (1) about said longitudinal axis (6); and (iv) a means (11) for gauging the insertion depth of said guide pin in said bone fragments. Said instrument (1), which is conveniently inserted onto said guide pin and rotatably moved, enables either the boring of at least one of the bone fragments by means of said cutting edges (20, 21), or the screwing of said cannulated screw, inserted onto said guide pin, by engaging with said nesting structure (15).

20 Claims, 4 Drawing Sheets

(51) Int. Cl.
*A61B 17/16* (2006.01)
*B25B 15/00* (2006.01)
*A61B 19/00* (2006.01)

(52) U.S. Cl.
CPC ........ *A61B 17/8877* (2013.01); *A61B 17/8894* (2013.01); *A61B 17/8897* (2013.01); *B25B 15/001* (2013.01); *A61B 17/1615* (2013.01); *A61B 2019/462* (2013.01)

(56) References Cited

U.S. PATENT DOCUMENTS

| | | | | |
|---|---|---|---|---|
| 4,092,753 | A | * | 6/1978 | Fuhrmann .......................... 7/158 |
| 5,411,523 | A | * | 5/1995 | Goble ........................... 606/232 |
| 5,425,733 | A | * | 6/1995 | Schmieding ................... 606/104 |
| 5,707,373 | A | * | 1/1998 | Sevrain et al. ................ 606/916 |
| 5,827,285 | A | * | 10/1998 | Bramlet ........................... 606/60 |
| 6,168,631 | B1 | * | 1/2001 | Maxwell et al. ............ 623/21.18 |
| 6,436,100 | B1 | * | 8/2002 | Berger ........................... 606/916 |
| 6,827,722 | B1 | * | 12/2004 | Schoenefeld ................. 606/104 |
| 7,207,995 | B1 | * | 4/2007 | Vandewalle ................... 606/104 |
| 2005/0209592 | A1 | * | 9/2005 | Schlapfer et al. ............... 606/60 |
| 2005/0222575 | A1 | * | 10/2005 | Ciccone et al. ................ 606/104 |
| 2006/0100627 | A1 | * | 5/2006 | Stone et al. ..................... 606/72 |
| 2006/0155297 | A1 | * | 7/2006 | Ainsworth et al. ............. 606/99 |
| 2007/0191852 | A1 | * | 8/2007 | Shimko et al. .................. 606/79 |
| 2009/0187194 | A1 | * | 7/2009 | Hamada ......................... 606/104 |
| 2009/0228015 | A1 | * | 9/2009 | Ellis et al. ........................ 606/87 |
| 2010/0241124 | A1 | * | 9/2010 | Housman et al. ............... 606/80 |
| 2010/0256688 | A1 | * | 10/2010 | Giersch et al. ................ 606/305 |
| 2010/0268242 | A1 | * | 10/2010 | Ciccone et al. ................ 606/104 |
| 2011/0238069 | A1 | * | 9/2011 | Zajac et al. ...................... 606/79 |
| 2011/0301614 | A1 | * | 12/2011 | Impellizzeri ................... 606/104 |
| 2012/0095515 | A1 | * | 4/2012 | Hamilton ....................... 606/304 |
| 2014/0276892 | A1 | * | 9/2014 | Pakzaban et al. .............. 606/104 |

* cited by examiner

SURGICAL INSTRUMENT FOR A TECHNIQUE FOR ATTACHING BONE FRAGMENTS USING A CANNULATED SCREW

The present invention relates to the field of surgical instruments used in osteosynthesis techniques. This invention more particularly relates to an instrument useful within the framework of operations of fixation of bone fragments by means of a cannulated screw, whose fitting is guided by a pin.

In the osteosynthesis techniques, it is common to use screws for fastening and compressing together two bone fragments. This method has the interest to realize a rapid osteosynthesis, with formation of a bone callus.

For the fastening of small fragments of bone, such as those of the toe and finger phalanxes, it is very often used a cannulated screw, whose implantation is guided by means of a pin.

To date, the fitting of this cannulated screw requires the use of a plurality of surgical instruments, commonly referred to as "ancillaries", each of which allow a particular operation in the surgical process.

In practice, the guiding pin, which is advantageously self-boring, is firstly placed through the two bone fragments to be fastened together.

Its depth of penetration is then measured by means of a first surgical instrument referred to as "gauge", so as to determine the length of the cannulated screw to be used.

After this measurement, the gauge is removed from the pin to leave the place to a cannulated reamer.

This second ancillary is engaged on the pin to realize, in the bone, a proximal bore for receiving a screw head.

Following the removing of the reamer, a cannulated screw is engaged on the pin and is actuated in rotation by means of a third surgical instrument consisting of a cannulated screwdriver.

This cannulated screw realizes simultaneously a boring and a tapping into the bone fragments, around the pin, in such a way to allow the progression thereof up to fully engage its head into the bone, and in particular into the above-mentioned bore.

The implantation of the cannulated screw then generates the fastening and the loading in compression of the bone fragments.

Once the cannulated screw in place, the pin may be removed from the bone fragments.

Hence, the surgical set or fitting kit provided to the practitioner very generally includes three cannulated ancillaries, each intended to cooperate with the guiding pin, i.e. a gauge, a reamer and a screwdriver.

This number of ancillaries to be used has the drawback to lengthen the duration of the intervention and to increase the cost of the fitting kit.

Moreover, when the fitting kit comprises screws with various diameters, the practitioner is likely to make a mistake when choosing one of the members of the gauge-reamer-screwdriver set adapted to the chosen screw.

The documents US-2005/0222575 and CH-634 742 describe similar surgical techniques, implemented by means of an instrumentation also using a plurality of ancillaries for the implementation of the various searched functionalities.

In this context, the applicant has developed a new surgical instrument that allows fulfilling the three above-mentioned functions linked to the fitting of a cannulated screw, i.e. (i) gauging the depth of penetration of the guiding pin into the bone fragments, (ii) boring at least one of the bone fragments to form a proximal bore for the reception of the head of the cannulated screw, and (iii) screwing the cannulated screw engaged on the guiding pin.

The use of such a surgical instrument has in particular the following advantages: gain of time for the practitioner, simplification of the fitting kit and limitation of the risk of error in the choice of the ad hoc instrument.

For that purpose, the surgical instrument according to the invention has an elongated cannulated body comprising:
 (i) a central channel defining a longitudinal axis, for the slidable and rotatable engagement of said instrument on the guiding pin,
 (ii) means for gauging the depth of penetration of said guiding pin into said bone fragments,
 (iii) a nesting structure, adapted to be inserted into an accommodation provided in the head of said cannulated screw and to lock them in rotation, and
 (iv) cutting edges, adapted to bore at least one of said bone fragments by rotation of said surgical instrument about its longitudinal axis, this instrument, suitably engaged on the guiding pin and operated in rotation, providing either the boring of at least one of said bone fragments by action of said cutting edges, or the screwing of said cannulated screw, engaged on said guiding pin, by cooperation with said nesting structure.

According to a preferred embodiment, a terminal part of the elongated cannulated body includes the nesting structure, and at least certain of the cutting edges are provided directly on this nesting structure.

According to this preferred embodiment, the terminal part advantageously includes at least two segments: (i) a distal segment, juxtaposed to the front end, which constitutes the nesting structure, inscribed in cylindrical volume of constant or at least approximately constant diameter, and (ii) a proximal segment, located remote from said front end, which is composed, in the distal to proximal direction, of a divergent truncated part and a cylindrical part whose diameter is constant, or at least approximately constant, and is higher than the diameter of the distal segment; furthermore, the cutting edges extend over each of these two distal and proximal segments.

In this case, the distal segment has advantageously an external surface consisted of several sides, defining together a polygonal cross-section; and the cutting edges are consisted by recesses provided in at least certain of said sides.

The corresponding recesses are advantageously each composed of two faces:
 (i) a transverse face, extending in a plane parallel to the longitudinal axis and the external border of which constitutes a cutting edge, and
 (ii) an inclined face, comprising—a distal end, located at the front end of the elongated body, and—a proximal end, connected to said transverse face and located remote from said front end.

The recesses of the distal segment are advantageously each provided within at least two juxtaposed sides, preferably within two or three juxtaposed sides.

Still preferably, these recesses of the distal segment open out at the front end, go through said distal segment to the central channel and extend over only a part of the length of the latter.

Moreover, the sides of the distal segment are advantageously divergent in the distal to proximal direction, to fulfill a function of prehensile clamp in the accommodation of the screw head.

According to still another characteristic of implementation, the cutting edges of the proximal segment advantageously extend, at least, over at least a part of the length of the truncated part and over at least a part of the length of the cylindrical part.

The cutting edges of the proximal segment in question advantageously consist in recesses each including two planar faces, squared with respect to each other, and each extending in a plane parallel to the longitudinal axis.

In this case, the distal segment advantageously comprises a distal end and a proximal end; and the two faces of the recesses of the proximal segment are connected by an edge provided in a plane that is radial with respect to the longitudinal axis and that extends at a distance from said longitudinal axis whose value is lower than or equal to the diameter of said proximal end of the distal segment.

More generally, the recesses at the level of the proximal segment and of the distal segment are advantageously in number of 2 to 4, preferably in number of 3, spaced apart from each other by a constant angular sector.

In this case, the distal segment has advantageously an outer surface consisted of six sides, in which are provided three recesses extending over at least two juxtaposed sides (preferably, over two or three juxtaposed sides) and offset relatively to each other by an angle of 120°.

On the other hand, the distal segment and the proximal segment are advantageously connected by an intermediate segment comprising a smooth cylindrical surface, whose diameter corresponds to the diameter of the distal segment.

Besides, the body of the instrument includes, opposite to the nesting structure, a structure for the removable fixation of a member for its rotational operation (manual or motorized), once engaged on the guiding pin.

The present invention still relates to a surgical set or kit, for a technique of fixation of bone fragments by means of a cannulated screw whose implantation is guided by a pin, said surgical set comprising at least one surgical instrument as defined hereinabove, advantageously associated with a range of cannulated screws, and with at least one guiding pin.

The invention will still be illustrated, without being limited in anyway, by the following description of a particular embodiment, in relation with the appended drawings in which.

The surgical instrument 1 according to the invention, illustrated in FIGS. 1 to 4, is intended to be used, as detailed in FIGS. 5 to 10, within the framework of a technique of fixation of bone fragments Fp and Fd (generally designated by the reference character F), by means of a cannulated screw V whose implantation is guided by a pin B (of conventional structure, having for example a constant diameter).

The cannulated screw V is advantageously of the self-compressive, self-boring and self-tapping type. It comprises in particular a proximal head V1 comprising an accommodation (not visible) adapted to receive the tip of a screwdriver, for its rotational operation.

This surgical technique is in particular useful for fastening together small bone fragments, such as those of the toe and finger phalanxes, following a fracture, or those coming from a corrective osteotomy (in particular for the treatment of a valgus hallux).

The surgical instrument 1, still referred to as "ancillary", is intended to be slidably and rotatably engaged on the guiding pin B, implanted on the bone fragments F, to fulfill three functions:
  (i) measuring the depth of penetration of the pin B in the bone fragments F,
  (ii) boring at least one of the bone fragments F (in particular a proximal bone fragment), for the reception of the head V1 of the cannulated screw V, and
  (iii) screwing in the bone the cannulated screw V that has been previously engaged on the guiding pin B.

Figures 1, 2:
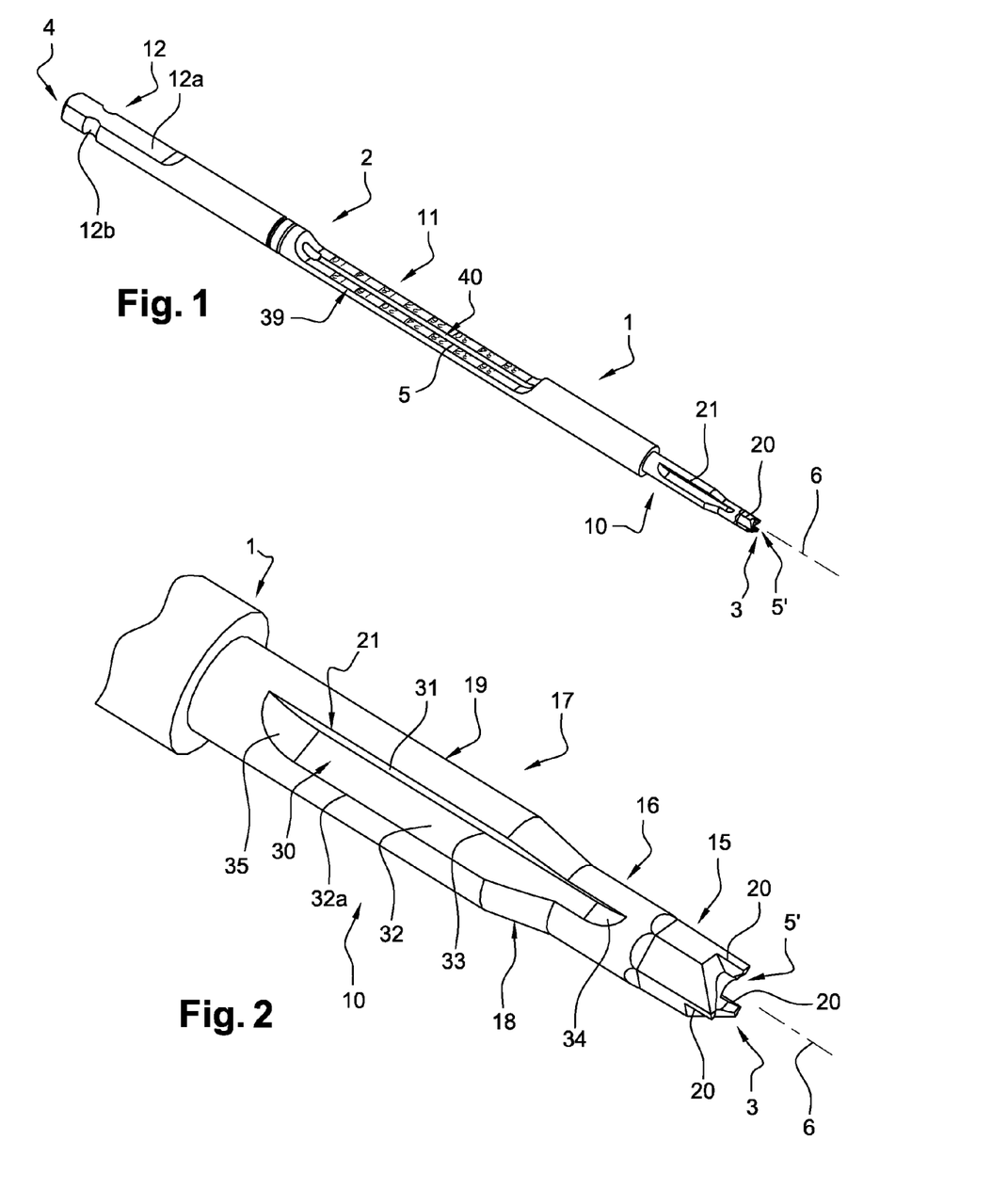
FIG. 1 is a general perspective view of the surgical instrument according to the invention.
FIG. 2 is a partial and enlarged view of the surgical instrument according to FIG. 1, illustrating its front terminal part at which are provided the nesting structure and the cutting edges.

As shown in FIG. 1, this surgical instrument 1 includes a one-piece elongated body 2, generally rod-shaped, delimited by two ends, i.e. a front end 3 and a rear end 4.

Generally, the "front" or "distal" term refers to a part of the instrument 1, of the cannulated screw V or of the pin B, which enters the first into contact with the bone.

The "rear" or "proximal" term corresponds to a part of this same instrument 1, of the cannulated screw V or of the pin B, which is located on the other side with respect to said front/distal part.

The elongated body 2 comprises a central channel 5, generally cylindrical in shape and of constant diameter, which opens out through a distal opening 5' located at the front end 3.

The central channel 5 extends along a longitudinal axis 6, passing through the two ends 3 and 4 of the elongated cannulated body 2.

This central channel 5 is so sized to receive coaxially a guiding pin B, so as to allow the guiding in translation and in rotation of the instrument 1 on this pin B.

Within this framework, the diameter of this central channel 5 advantageously corresponds, to within the clearance, to the outer diameter of the guiding pin B.

Figure 7:
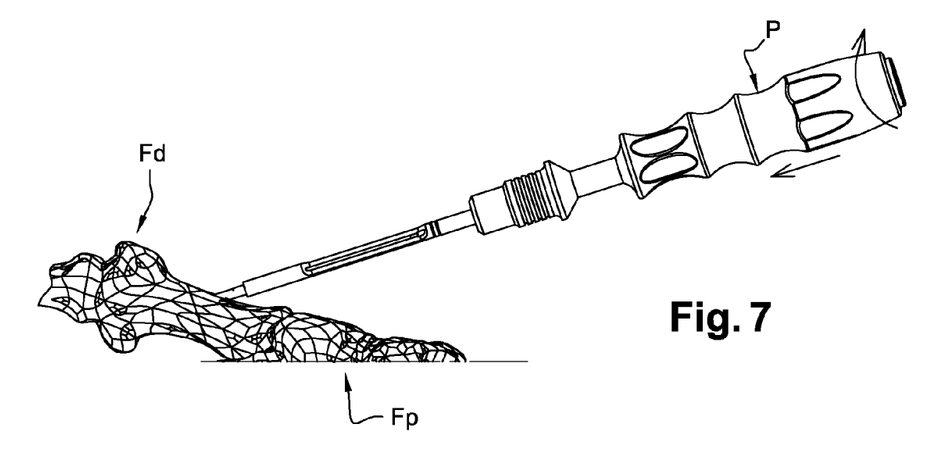

To fulfill the various searched functionalities, the elongated cannulated body 2 is divided into three parts, respectively distributed from its front end 3 to its rear end 4, i.e.:
  (i) a front terminal part 10, to bore the bone fragments F and to cooperate with the head V1 of the cannulated screw V,
  (ii) an intermediate part 11, to gauge the depth of penetration of the guiding pin B into the bone fragments F, and
  (iii) a rear terminal part 12, adapted so as to removably receive a member (P) for the rotational operation of the instrument 1 engaged on the guiding pin B (FIG. 7).

The front terminal part 10 is illustrated in more details in FIG. 2.

This front terminal part 10 herein includes three coaxial segments, i.e., from the front end 3:
  (i) a distal segment 15, on the side of said front end 3, which constitutes simultaneously,—a structure for boring in the bone material, and—a nesting structure adapted to be inserted in an accommodation provided in the head V1 of the cannulated screw V and to lock them in rotation,
  (ii) an optional, intermediate segment 16 having a circular cylindrical surface, and
  (iii) a proximal segment 17, located remote from the front end 3, which is composed, in the distal to proximal direction, of a divergent truncated part 18 and of a circular cylindrical part 19.

The front terminal part 10 also includes a plurality of cutting edges 20 and 21, respectively provided on the distal segment 15 and on the intermediate 16/proximal 17 segments.

These cutting edges 20 and 21 are so shaped for boring the bone fragments F during the rotation of the surgical instrument 1 about its longitudinal axis 6.

Figure 3:
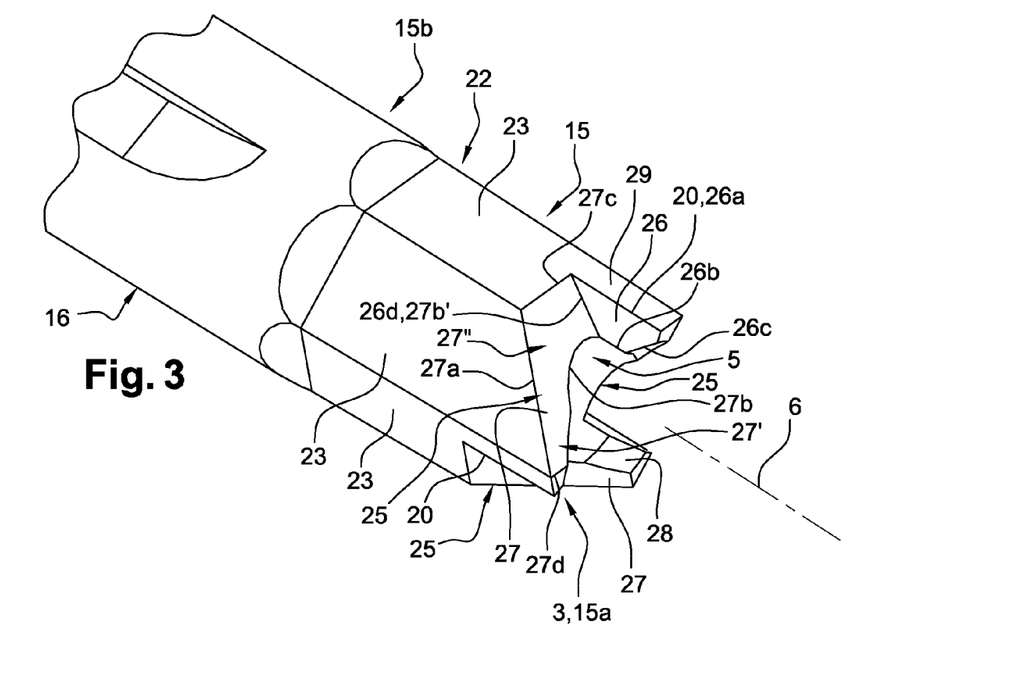
FIG. 3 is an enlarged view of FIG. 2, showing in detail the structure of the distal segment of the front terminal part.
Figure 4:
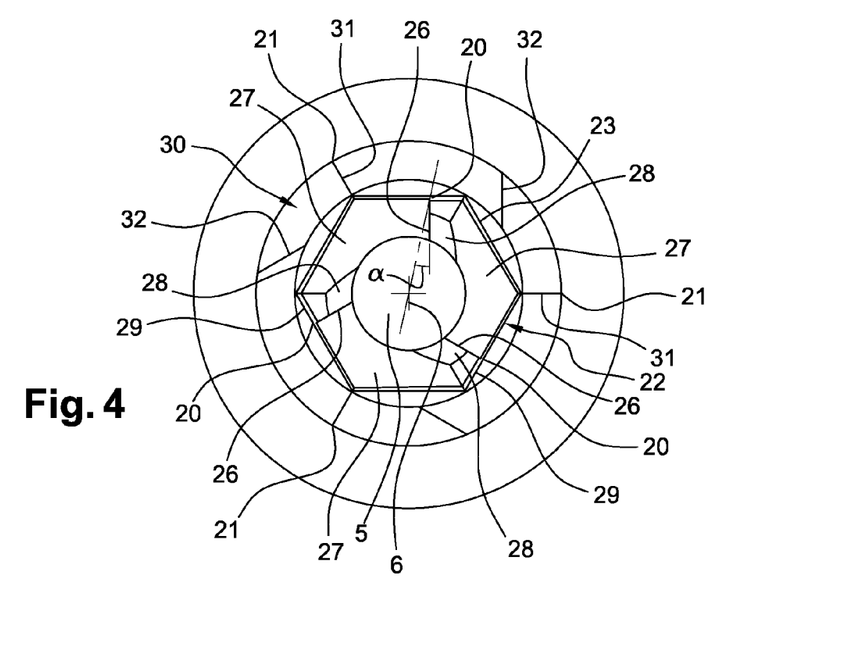
FIG. 4 is an enlarged representation of the surgical instrument of FIGS. 1 to 3, viewed axially at its front end.

FIGS. 3 and 4 show in more detail the distal segment 15.

This distal segment 15 is delimited—by a distal end 15a, located on the side of the front end 3 of the elongated body 2, and—by a proximal end 15b, remote from said front end 3.

This distal segment 15 has an outer surface 22 consisted of several sides 23 defining together a polygonal cross-section. These sides 23, herein in number of six, thus define an outer surface 22 of hexagonal section.

The distal segment 15 is inscribed in a cylindrical volume, approximately constant in diameter over its length.

More precisely, the sides 23 of this distal segment 15 are slightly divergent from the distal end 15a to the proximal end 15b.

This particular shape allows fulfilling a function of prehensile clamp in the accommodation of the head V1 of the cannulated screw V.

By way of indication, the divergence of these sides 23 of the distal segment 15 is advantageously comprised between 1° and 3°.

The cutting edges 20, in distal position, are consisted by recesses 25 provided in the thickness of the distal segment 15.

The recesses 25 are herein in number of three, offset with respect to each other by an angle of 120°.

These recesses 25 open out at the front end 3 of the elongated body 2, they go through the distal segment 15 to the central channel 5 and extend over only a part of the height of this distal segment 15.

More precisely, each recess 25 is composed of two faces arranged in a dihedral manner and provided within two juxtaposed sides 23, i.e.:
  (i) a transverse face 26, approximately radial, extending in a plane parallel to the longitudinal axis 6 and provided in a first side 23 of the distal segment 15, and
  (ii) an inclined face 27, oriented toward the front end 3, extending in a plane which is perpendicular to said transverse face 26 and inclined with respect to a plane perpendicular to the axis 6, to generate the relief angle required for obtaining a cutting effect.

The transverse face 26 is provided in a first side 23 of the distal segment 15. The inclined face 27 is provided within said first side 23 and also extends into the juxtaposed side 23.

The transverse face 26 of a recess 25 and the inclined face 27 of a juxtaposed recess 25 are connected to each other by two faces, i.e.:
  a bevelled inner face 28, opposite the longitudinal axis 6, which diverges toward the outside in the proximal to distal direction, and
  an outer face 29, corresponding to a distal part of a side 23 of the distal segment 15.

The bevelled inner faces 28 delimit together a truncated volume, diverging in the proximal to distal direction, to facilitate the initiation of the insertion of the pin B within the central channel 5 of the instrument 1, and the insertion of the ancillary into the bone during the boring operation.

In FIG. 4, it can be observed that the transverse face 26 of each recess 25 forms a positive angle α with respect to a radiant plane passing through its cutting edge 20.

By way of indication, this angle α is advantageously comprised between 3° and 10°.

This transverse face 26 has a generally trapezoid shape, which is delimited (FIG. 3):
  by a rectilinear outer border 26a connected to one of the outer faces 29, arranged parallel to the longitudinal axis 6 and forming the cutting edge 20 of the recess 25,
  by a rectilinear inner border 26b, arranged parallel to the longitudinal axis 6,
  by a distal border 26c, including a part diverging toward the outside in the proximal to distal direction, and
  by a proximal border 26d, diverging toward the outside in the distal to proximal direction, forming the edge of connection with the inclined face 27 of the same recess 25.

This transverse face 26 thus constitutes a cutting face; and the associated outer face 29 constitutes a relief face.

The inclined face 27 has—a distal free end 27', located at the front end 3 of the elongated body 2, and—a proximal end 27", connected to said planar face 26 and located remote from said front end 3.

The inclined face 27 extends herein in a plane forming an angle comprised between 45° and 60° with respect to the longitudinal axis 6.

This inclined surface 27 is delimited:
  by a rectilinear outer border 27a, going progressively away from the front end 3 of the elongated body 2, starting from the distal end 27',
  by an inner border 27b, a portion 27b' of which is merged with the proximal border 26d of the transverse face 26, to form the connection edge,
  by a proximal border 27c, extending square to the longitudinal axis 6 and remote from the front end 3 of the elongated body 2, and
  by a distal border 27d, extending square to the longitudinal axis 6 and located at the front end 3 of the elongated body 2.

The outer edge 26a of the transverse face 26 and the proximal edge 27c of the inclined face 27 define together a square, or at least approximately square, angle.

Such a recess structure is in particular adapted to the machining constraints.

The intermediate segment 16 extends the proximal end 15b of the distal segment 15.

This intermediate segment 16 has a generally cylindrical shape whose external diameter is constant over its length and corresponds to the diameter of the proximal end 15b of the distal segment 15.

This intermediate segment 16 is useful in particular for the operations of fabrication of the elongated body 2, so as to take into account the machining constraints.

The proximal segment 17 is illustrated in particular in FIG. 2.

The divergent truncated part 18 of this proximal segment 17 has advantageously a slope of the order of 13° to 17°, and preferably of the order of 15°

The cylindrical part 19 has a diameter that is higher than the general diameter of the distal segment 15 and of the intermediate segment 16. The diameter of this cylindrical part 19 is adapted to that of the head V1 of the screw V to be fitted.

The cutting edges 21 of this proximal segment 17 are formed by recesses 30 provided in its thickness; these recesses 30 herein continue over a part of the length of the intermediate segment 16.

The cutting edges 21, in proximal position, hence each extend over the cylindrical part 19, the truncated part 18 and the intermediate segment 16.

The cutting edges 21 of this proximal segment 17 are also in number of three; the corresponding recesses 30 are thus offset with respect to each other by an angle of the order of 120°.

The cutting edges 21 of the proximal segment 17 are offset, or aligned, with respect to the cutting edges 20 of the distal segment 15.

The recesses 30 are generally dihedral in shape, and are each composed of two planar surfaces 31 and 32 that are connected by a connection edge 33.

The planar faces 31 and 32 of each recess 30 extend square relative to each other, and each in a plane parallel to the longitudinal axis 6.

More precisely, a first face 31 of the recess 30 extends in a plane passing through the longitudinal axis 6 (FIG. 4).

This first planar face 31 is delimited—by an outer longitudinal border corresponding to the cutting edge 21, and—by an inner longitudinal border corresponding to the connection edge 33.

This first planar face 31 constitutes a cutting edge.

The second face 32 of the recess 30 is delimited—by an outer border 32a, and—by an inner longitudinal border corresponding to the connection edge 33.

The connection edge 33 is provided parallel to the longitudinal axis 6.

The radius defined between each connection edge 33 and the axis 6 is smaller than the outer radius defined by the distal 15 and intermediate 16 segments, with respect to the same axis 6.

On the other hand, the second face 32 is ended by two concave curved portions, i.e. a distal curved portion 34 and a proximal curved portion 35, at its distal end and its proximal end, respectively.

These curved portions 34 and 35 diverge toward the outside, in the proximal to distal direction for the distal curved portion 34, and in the distal to proximal direction for the proximal curved portion 35.

Besides, as shown in FIG. 1, the depth gauge part 11 herein consists in a notch 39 provided in the thickness of the elongated cannulated body 2 to form a window 40 through which the central channel 5 is directly visually accessible to the practitioner.

On either side of this window 40, the notch 39 is provided with a set of graduations of the length-mark type, which are suitably distributed to determine the depth of penetration of the guiding pin B in the bone fragments F.

More precisely, these graduations are decreasing in the distal to proximal direction. The length of the screw V to be used is read directly through the window 40, and corresponds to the graduation juxtaposed to the free proximal end of the guiding pin B.

The central channel 5 is blind, in that it is ended at the gauge part 11 and does not continue within the rear terminal part 12.

As also shown in FIG. 1, the rear terminal part 12 is generally cylindrical in shape, with a flat 12a and an annular groove 12b provided at this flat 12a.

This particular shape of the rear terminal part 12 is in particular adapted to removably receive a manual operation member of the screwdriver-handle type P, as shown in FIG. 7.

The implementation of this surgical instrument 1 is described in more detail hereinafter in relation with FIGS. 5 to 10.

Figure 5:
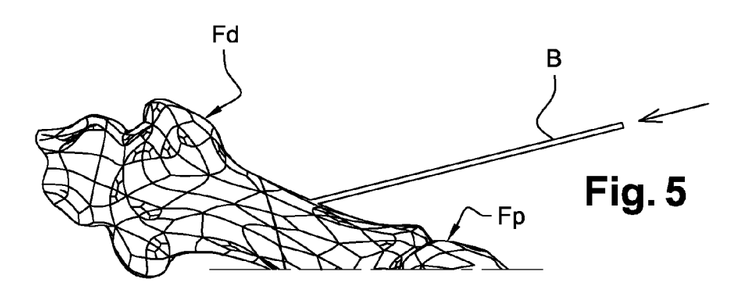
FIGS. 5 to 10 show the main steps of implementation during the fitting of a cannulated screw on the two bone fragments to be linked, by means of the surgical instrument according to FIGS. 1 to 4.

Firstly, as illustrated in FIG. 5, the guiding pin B is fitted through the two bone fragments to be fastened together, i.e. a proximal bone fragment Fp and a distal bone fragment Fd.

This guiding pin B is for example inserted by means of a device of the surgical motor type.

To measure the length of the screw V to be used, the practitioner then slidably engages the surgical instrument 1 over the length of the guiding pin B, by introduction of this pin B within the central channel 5 thereof.

Figure 6:
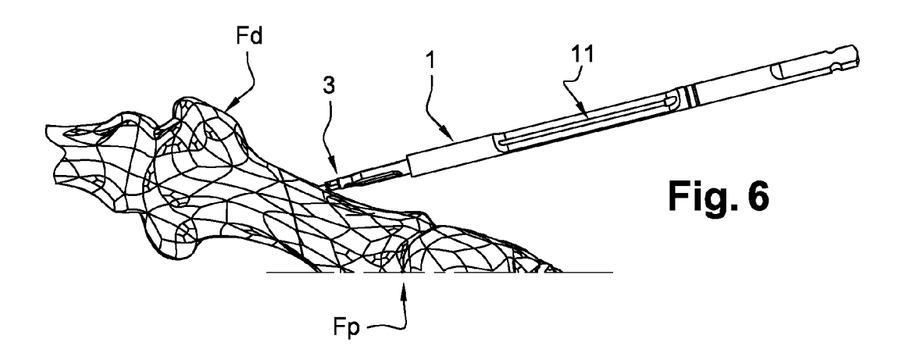

The surgical instrument 1 is operated by translation on the guiding pin B, until its front end 3 comes into abutment with the proximal bone fragment Fp (FIG. 6).

The surgeon may then read the depth of penetration of the pin B at the depth gauge part 11 of the instrument 1, and deduce therefrom the length of the screw he/she has to fit.

Following this reading, the surgeon operates the surgical instrument 1 in rotation on the guiding pin B, while exerting a thrust toward the bone fragments F (FIG. 7).

This operation of the surgical instrument 1 allows boring the bone fragments F, and in particular the proximal bone fragment Fp, by the action of the cutting edges 20 and 21 provided at the front terminal part 10.

In practice, the distal cutting edges 20 generate a first bore of small diameter in the bone material; and the proximal cutting edges 21 thereafter widen this bore, so that its size is adapted to the head V1 of the screw V to be fitted.

To facilitate this operation, the surgical instrument 1 is advantageously equipped with the prehensile handle P at the rear terminal part 12.

This boring then allows to provide a proximal bore intended to receive the head V1 of the cannulated screw V.

Once the bone suitably bored, the instrument 1 is extracted from the guiding pin B, by a rearward translation.

Figure 8:
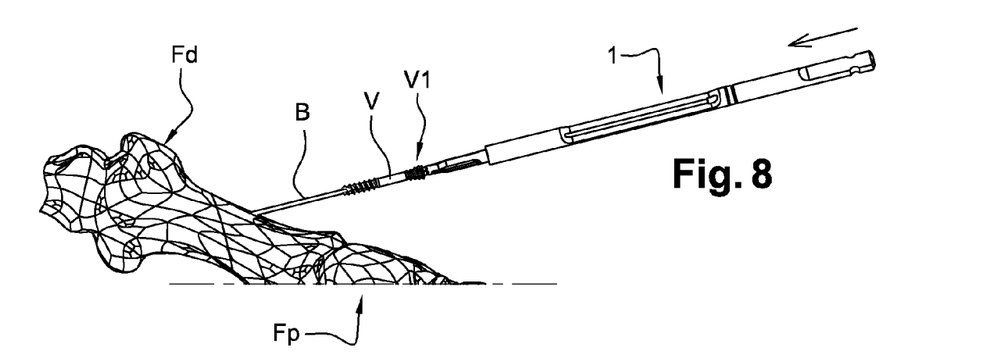

The practitioner may then add successively the cannulated screw V and again the same surgical instrument 1, on the guiding pin B (FIG. 8).

The cannulated screw V herein consists in a self-compressive screw, with self-boring and self-tapping functionalities. This screw V is chosen with a length accurate to that obtained during the preceding step of measurement with the dedicated means 11.

The distal segment 15 of the surgical instrument 1 is nested into the accommodation of the head V1 of the cannulated screw V.

During this cooperation, the six sides 23 of this distal segment 15 ensure the locking in rotation of the instrument 1 and of the cannulated screw V.

Figure 9:
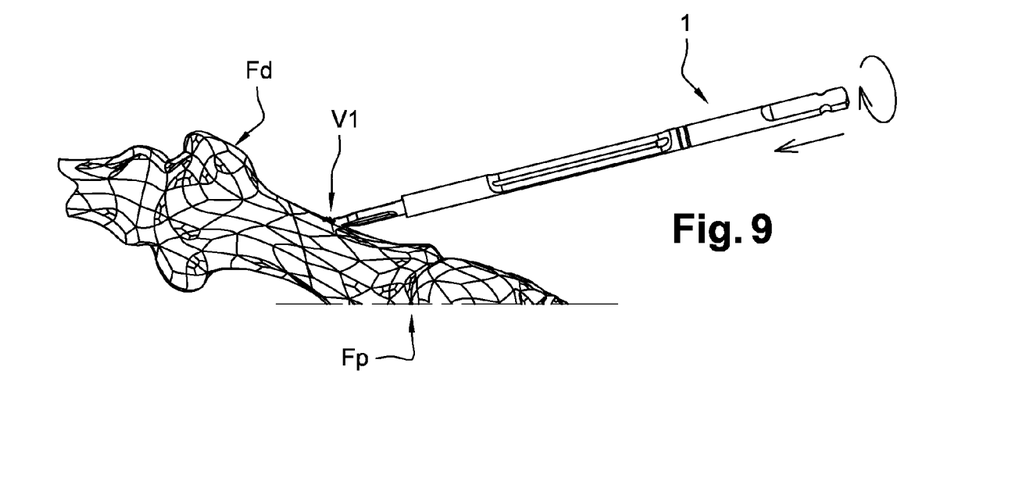

The rotational operation, with forward thrust, of the surgical instrument 1 then allows the cannulated screw V, also actuated in rotation and in translation, to realize simultaneously a boring and a tapping into the bone about the guiding pin B, and to allow its fitting into the two bone fragments F (FIG. 9).

During this operation, the surgical instrument 1 and the screw V are guided in translation and in rotation by the pin B.

This screwing operation is continued until the head V1 of the screw V is fully embedded in the bone (FIG. 9). It is advantageously realized by means of the handle P, even if the latter is not shown in FIGS. 8 and 9.

Figure 10:
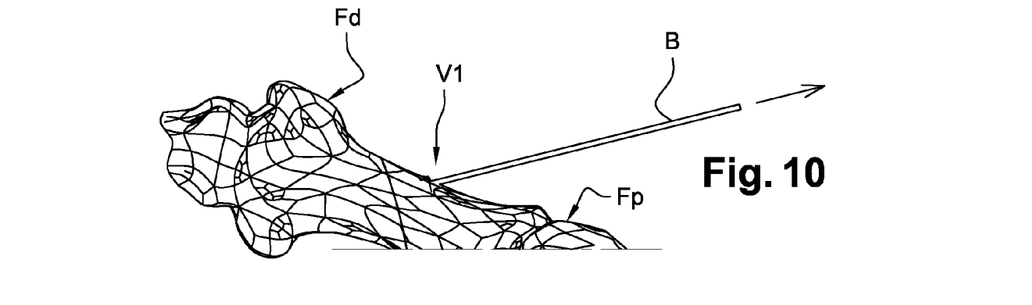

This engagement completed, the guiding pin B may be removed from the two bone fragments Fp and Fd, by an adapted axial traction (FIG. 10).

The use of such a surgical instrument allows time gains for the practitioner, which may use a single ancillary all along the fitting of the screw.

Moreover, the fitting kit is simplified thanks to this 3-in-1-type ancillary. When several types of screws are available in this fitting kit, the ancillary according to the invention also allows limiting the errors in the choice of instrument families.

The invention claimed is:

1. A surgical instrument for fixation of bone fragments by a cannulated screw whose implantation is guided by a guiding pin,
wherein said surgical instrument has an elongated cannulated body comprising:
a central channel defining a longitudinal axis, the central channel being adapted to slidably and rotatably engage said instrument on said guiding pin, and
a nesting structure adapted to be inserted in an accommodation provided in a head of said cannulated screw, so as to lock the surgical instrument and the cannulated screw in rotation,
wherein said elongated cannulated body comprises:
cutting edges adapted to bore at least one of said bone fragments by rotating said surgical instrument about said longitudinal axis, and
a depth gauge part adapted to gauge a depth of penetration of said guiding pin into said bone fragments,
so that said surgical instrument, when engaged on said guiding pin and rotated, performs at least one of (i) boring of at least one of said bone fragments by action of said cutting edges, and (ii) screwing of said cannulated screw, engaged on said guiding pin, by cooperation with said nesting structure.

2. The surgical instrument according to claim 1, wherein a terminal part of the elongated cannulated body includes the nesting structure, and at least one of said cutting edges is provided directly on said nesting structure.

3. The surgical instrument according to claim 2,
wherein the elongated cannulated body has a front end and a rear end, and
wherein the terminal part of the elongated body comprises at least two segments:
(i) a distal segment juxtaposed to said front end, wherein said distal segment constitutes the nesting structure, and wherein said distal segment is inscribed in a cylindrical volume of constant or at least approximately constant diameter, and
(ii) a proximal segment located at a distance from said front end, wherein said proximal segment comprises, in a distal to proximal direction, divergent truncated part and a cylindrical part, wherein a diameter of the cylindrical part is at least approximately constant, and is higher than a diameter of the distal segment,
and said cutting edges extend over each of said distal and proximal segments.

4. The surgical instrument according to claim 3,
wherein the distal segment comprises an outer surface comprising a plurality of sides, the plurality of sides defining a polygonal cross-section, and
wherein recesses provided in at least one of said sides define the cutting edges at the distal segment.

5. The surgical instrument according to claim 4, wherein the recesses each comprises:
(i) a transverse face which extends in a plane parallel to the longitudinal axis and which comprises an outer border that defines a cutting edge, and
(ii) an inclined face, having
a distal end located at the front end of the elongated cannulated body, and
a proximal edge connected to said transverse face and located at a distance from said front end.

6. The surgical instrument according to claim 3, wherein the cutting edges of the proximal segment extend over at least a part of a length of the divergent truncated part and over at least a part of a length of the cylindrical part.

7. The surgical instrument according to claim 3,
wherein the proximal segment comprises a plurality of recesses that define the cutting edges of the proximal segment,
wherein each of the plurality of recesses comprises two planar faces which are perpendicular with respect to each other, and
wherein each of the two planar faces extends in a plane parallel to the longitudinal axis.

8. The surgical instrument according to claim 7,
wherein the distal segment comprises a distal end and a proximal end, and the two planar faces of the recesses of the proximal segment are connected by a connecting edge provided in a plane that is radial with respect to the longitudinal axis,
wherein the connecting edge extends at a distance from said longitudinal axis, and
wherein the distance between the connecting edge and the longitudinal axis is lower than or equal to a diameter of said proximal end of the distal segment.

9. The surgical instrument according to claim 3,
wherein each of the proximal segment and the distal segment comprises 2 to 4 recesses, and
wherein the recesses are spaced apart from each other by a constant angular sector.

10. The surgical instrument according to claim 1, wherein the elongated cannulated body of the surgical instrument comprises, opposite to the nesting structure, a structure adapted to removably receive a member for rotational operation of said surgical instrument engaged on the guiding pin.

11. A surgical set comprising:
the surgical instrument according to claim 1,
at least one cannulated screw, and
at least one guiding pin,
for fixation of bone fragments by said cannulated screw whose implantation is guided by said guiding pin.

12. The surgical instrument according to claim 4, wherein the cutting edges of the proximal segment extend over at least a part of a length of the divergent truncated part and over at least a part of a length of the cylindrical part.

13. The surgical instrument according to claim 5, wherein the cutting edges of the proximal segment extend over at least a part of a length of the divergent truncated part and over at least a part of a length of the cylindrical part.

14. The surgical instrument according to claim 4,
wherein the proximal segment comprises a plurality of recesses that define the cutting edges of the proximal segment,
wherein each of the plurality of recesses comprises two planar faces which are perpendicular with respect to each other, and
wherein each of the two planar faces extends in a plane parallel to the longitudinal axis.

15. The surgical instrument according to claim 5,
wherein the proximal segment comprises a plurality of recesses that define the cutting edges of the proximal segment,
wherein each of the plurality of recesses comprises two planar faces which are perpendicular with respect to each other, and
wherein each of the two planar faces extends in a plane parallel to the longitudinal axis.

16. The surgical instrument according to claim 6,
wherein the proximal segment comprises a plurality of recesses that define the cutting edges of the proximal segment, wherein each of the plurality of recesses comprises two planar faces which are perpendicular with respect to each other, and
wherein each of the two planar faces extends in a plane parallel to the longitudinal axis.

17. The surgical instrument according to claim 12,
wherein the proximal segment comprises a plurality of recesses that define the cutting edges of the proximal segment,
wherein each of the plurality of recesses comprises two planar faces which are perpendicular with respect to each other, and
wherein each of the two planar faces extends in a plane parallel to the longitudinal axis.

18. The surgical instrument according to claim 13,
wherein the proximal segment comprises a plurality of recesses that define the cutting edges of the proximal segment,
wherein each of the plurality of recesses comprises two planar faces which are perpendicular with respect to each other and
wherein each of the two planar faces extends in a plane parallel to the longitudinal axis.

19. The surgical instrument according to claim 14,
wherein the distal segment comprises a distal end and a proximal end, and the two planar faces of the recesses of the proximal segment are connected by a connecting edge provided in a plane that is radial with respect to the longitudinal axis,
wherein the connecting edge extends at a distance from said longitudinal axis, and
wherein the distance between the connecting edge and the longitudinal axis is lower than or equal to a diameter of said proximal end of the distal segment.

20. The surgical instrument according to claim 15,
wherein the distal segment comprises a distal end and a proximal end, and the two planar faces of the recesses of the proximal segment are connected by a connecting edge provided in a plane that is radial with respect to the longitudinal axis,
wherein the connecting edge extends at a distance from said longitudinal axis, and
wherein the distance between the connecting edge and the longitudinal axis is lower than or equal to a diameter of said proximal end of the distal segment.

* * * * *